(12) United States Patent
McDermott

(10) Patent No.: US 9,289,608 B2
(45) Date of Patent: Mar. 22, 2016

(54) DEVICE AND CIRCUITRY FOR CONTROLLING DELIVERY OF STIMULATION SIGNALS

(75) Inventor: Hugh Joseph McDermott, Mt Macedon (AU)

(73) Assignee: The Bionics Institute of Australia (AU)

( * ) Notice: Subject to any disclaimer, the term of this patent is extended or adjusted under 35 U.S.C. 154(b) by 0 days.

(21) Appl. No.: 14/235,696

(22) PCT Filed: Jul. 25, 2012

(86) PCT No.: PCT/AU2012/000879
§ 371 (c)(1),
(2), (4) Date: Jun. 24, 2014

(87) PCT Pub. No.: WO2013/013265
PCT Pub. Date: Jan. 31, 2013

(65) Prior Publication Data
US 2014/0303691 A1 Oct. 9, 2014

Related U.S. Application Data

(60) Provisional application No. 61/512,752, filed on Jul. 28, 2011.

(51) Int. Cl.
*A61N 1/00* (2006.01)
*A61N 1/36* (2006.01)
*A61N 1/05* (2006.01)

(52) U.S. Cl.
CPC ........ *A61N 1/36128* (2013.01); *A61N 1/36003* (2013.01); *A61N 1/36032* (2013.01); *A61N 1/36046* (2013.01); *A61N 1/36175* (2013.01); *A61N 1/0541* (2013.01); *A61N 1/0543* (2013.01)

(58) Field of Classification Search
CPC ............ A61N 1/3605; A61N 1/36014; A61N 1/36128; A61N 1/36175; A61N 1/36146; A61N 1/36125
See application file for complete search history.

(56) References Cited

U.S. PATENT DOCUMENTS 6,253,103 B1   6/2001  Baura
2006/0247739 A1  11/2006  Wahlstrand et al.
(Continued)

FOREIGN PATENT DOCUMENTS

WO   WO-2008/049199   5/2008

OTHER PUBLICATIONS

"International Application No. PCT/AU2012/000879, Demand and Article 34 Amendmentmailed May 24, 2013", 12 pgs.
"International Application No. PCT/AU2012/000879, International Preliminary Report on Patentability mailed Nov. 10, 2013", 41 pgs.
"International Application No. PCT/AU2012/000879, International Search Report and Written Opinion mailed Aug. 30, 2012", 15 pgs.
"International Application No. PCT/AU2012/000879, Second Written Opinion of the International Preliminary Examining Authority mailed Jul. 10, 2013", 7 pgs.

*Primary Examiner* — Robert N Wieland
(74) *Attorney, Agent, or Firm* — Schwegman Lundberg & Woessner, P.A.

(57) ABSTRACT

Embodiments relate to a device for controlling delivery of stimulation signals, comprising: a stimulation delivery circuit; a monitoring component to monitor voltage supplied in at least one current-driven charge pulse via the stimulation delivery circuit; and a stimulation control component to control voltage supplied in at least one subsequent charge pulse based on the charge of the at least one charge pulse delivered by the stimulation delivery circuit. The device may further comprise a model generation component to generate an impedance model of stimulation electrodes in the stimulation delivery circuit, wherein the stimulation control component is configured to control the stimulation delivery circuit to deliver charge according to the impedance model.

20 Claims, 5 Drawing Sheets

(56) References Cited

U.S. PATENT DOCUMENTS

| | | |
|---|---|---|
| 2006/0253174 A1 | 11/2006 | King |
| 2010/0023070 A1* | 1/2010 | Moffitt et al. ............ 607/2 |
| 2011/0160799 A1* | 6/2011 | Mishra et al. ........... 607/57 |
| 2012/0277830 A1* | 11/2012 | Arfin et al. ............. 607/62 |

* cited by examiner

DEVICE AND CIRCUITRY FOR CONTROLLING DELIVERY OF STIMULATION SIGNALS

PRIORITY CLAIM TO RELATED APPLICATIONS

This application is a national stage application under 35 U.S.C. §371 of PCT/AU2012/000879, filed Jul. 25, 2012, and published as WO 2013/013265 on Jan. 31, 2013, which claims priority to U.S. Provisional Application Ser. No. 61/512,752, filed Jul. 28, 2011, which applications and publication are incorporated by reference as if reproduced herein and made a part hereof in their entirety, and the benefit of priority of each of which is claimed herein.

TECHNICAL FIELD

Described embodiments generally relate to devices, circuitry and prostheses for controlling delivery of stimulation signals for excitable tissue, such as nerves and muscles.

BACKGROUND

Biphasic current stimulation is widely used in electrical stimulation of neurons and other electrically excitable tissue. This constant-current form of stimulation has an advantage that the charge delivered by the stimulation is largely unaffected by changes in electrode impedance which occur at the interface between the signal conductors and the tissue.

The voltage required to stimulate an electrode is the product of the stimulation current and the electrode impedance in a similar way, to Ohms law, which states that the voltage across a resistance is equal to the product of resistance and current. In the case of a biological stimulating electrode, the impedance is not a pure resistance but has capacitive or capacitance-like properties. Electrode impedance varies from electrode to electrode and over time.

For constant-current stimulation using rectangular biphasic pulses, the so-called impedance is defined as the voltage at a stimulation electrode at the end of the first phase of a stimulation pulse divided by the electrode current. While Ohms law applies strictly to pure resistance, the same principle is applied to calculate the voltage required to obtain a particular stimulation current.

A disadvantage of using constant current to generate the biphasic stimulation signals is that the signal generation circuitry does not always generate sufficient voltage in order to deliver the desired amount of charge to the tissue. FIG. 1 is a graph of voltage required at the signal generation circuit versus percentage of electrodes operating within voltage compliance for adults and children using aural prostheses that employ biphasic current stimulation. FIG. 1 shows that for some situations, a larger voltage is required in order to deliver the necessary charge than for other situations. Additionally, it is evident from FIG. 1 that, for much of the time, the maximum voltage level is not required in order to achieve charge delivery compliance and so a lower voltage would suffice.

The provision of a higher voltage (i.e. around 10 volts) to cater for the relatively small number of occasions that it is needed results in a far higher power consumption than is actually delivered to the electrodes, with the rest being absorbed in the current source. This power consumption has a significant effect on battery life for prostheses employing biphasic current stimulation.

It is desired to address or ameliorate one or more shortcomings or disadvantages associated with prior techniques for delivery of biphasic stimulation to excitable tissue, such as nerves and/or muscles or to at least provide a useful alternative thereto.

SUMMARY

Some embodiments relate to a device for controlling delivery of stimulation signals, comprising:
a stimulation delivery circuit;
a monitoring component to monitor voltage supplied in at least one current-driven charge pulse via the stimulation delivery circuit; and
a stimulation control component to control voltage supplied in at least one subsequent charge pulse based on the charge of the at least one charge pulse delivered by the stimulation delivery circuit.

The device may further comprise a model generation component to generate an impedance model of stimulation electrodes in the stimulation delivery circuit, wherein the stimulation control component is configured to control the stimulation delivery circuit to deliver charge according to the impedance model. The model generation component may generate an impedance model in respect of each of a plurality of sets of electrodes, where a set of electrodes includes one or more electrodes. The model generation component may be configured to generate the impedance model based on measured voltage and controlled current delivery via the stimulation delivery circuit during the at least one charge pulse. The impedance model may be a RC circuit impedance model, for example.

The model generation component may be configured to periodically regenerate the impedance model based on a selected subsequently delivered current-driven charge pulse. The model generation component may be configured to use an adjustment model to adjust the pulse width or quantum of charge to be delivered in a charge pulse according to the impedance model. This adjustment is intended to keep the stimulation outcome consistent with the stimulation outcome that would have been achieved using the at least one current-driven charge pulse.

In some embodiments, the monitoring component may alternatively monitor current supplied in at least one voltage-driven charge pulse via the stimulation circuit. For such embodiments, the impedance model may be generated based on measured current and controlled voltage applied via the stimulation delivery circuit during the at least one charge pulse.

The device may further comprise a processor, wherein the model generation component comprises a code module accessible to the processor and executable by the processor. The monitoring component and stimulation control component may comprise code modules accessible to the processor and executable by the processor, and the processor may be configured to control delivery of charge by the stimulation delivery circuit.

Some embodiments relate to a device for controlling delivery of stimulation signals, comprising:
a stimulation delivery circuit;
a control component to control delivery of at least one initial charge pulse via the stimulation delivery circuit based on a first control parameter and to control delivery of at least one subsequent charge pulse via the stimulation delivery circuit based on a second control parameter; and
an adjustment component to modify controlled delivery of the at least one subsequent charge pulse based on an adjustment model.

The adjustment component may modify delivery of the at least one subsequent charge pulse by increasing or decreasing at least one pulse width of the at least one subsequent charge pulse.

Some embodiments relate to a device, for controlling delivery of stimulation signals, comprising:
a stimulation delivery circuit;
a control component to control delivery of at least one charge pulse via the stimulation delivery circuit based on an impedance model of a plurality of stimulation electrodes; and
an adjustment component to modify controlled delivery of the at least one charge pulse based on an adjustment model.

The adjustment component may modify delivery of the at least one charge pulse by increasing or decreasing at least one pulse width of the at least one charge pulse.

Some embodiments relate to a device for controlling delivery of stimulation signals, comprising:
means to generate an electrode impedance model for each of a plurality of sets of stimulation electrodes based on at least one initial charge pulse provided to each respective set of stimulation electrodes; and
means to control the provision of at least one subsequent charge pulse to one or more of the plurality of sets of stimulation electrodes based on the respective electrode impedance model generated for the one or more sets of stimulation electrodes.

The device may be configured for use as part of a prosthesis. The prosthesis may be a sensory prosthesis, such as an auditory or visual prosthesis. In other embodiments, the prosthesis may be a cardiac prosthesis or another prosthesis for delivering myoelectric stimulation. In some embodiments, the device may form part of a device for stimulation of a selected part of the brain, for example to modulate, hinder or otherwise beneficially affect various brain disorders, particularly including but not limited to movement disorders, psychiatric disorders, seizures or potential seizures. Such seizures may be associated with epilepsy or Parkinson's disease, for example.

Some embodiments relate to a prosthesis (or a similar type of medical bionics device) comprising the described device and/or configured to perform the described method.

Some embodiments relate to a method for controlling delivery of stimulation signals, the method comprising:
delivering at least one current-driven charge pulse, via a stimulation delivery circuit;
monitoring voltage supplied in the at least one charge pulse via the stimulation delivery circuit; and
controlling voltage supplied in at least one subsequent charge pulse based on the charge of the at least one charge pulse delivered by the stimulation delivery circuit.

The method may further comprise generating an impedance model of stimulation electrodes in the stimulation delivery circuit, wherein the controlling comprises controlling the stimulation delivery circuit to deliver charge according to the impedance model. An impedance model may be generated in respect of each of a plurality of sets of electrodes, where a set of electrodes includes one or more electrodes. The impedance model may be generated based on measured voltage and controlled current delivery via the stimulation delivery circuit during the at least one charge pulse. The impedance model may be a RC circuit impedance model, for example.

In some embodiments, the delivering may alternatively involve delivering at least one voltage-driven charge pulse and the monitoring may alternatively involve monitoring current supplied in the at least one voltage-driven charge pulse via the stimulation circuit. For such embodiments, the impedance model may be generated based on measured current and controlled voltage applied via the stimulation delivery circuit during the at least one charge pulse. Thus, embodiments are intended to encompass different ways of obtaining the necessary impedance values on which to generate the impedance model, whether using constant current or constant voltage as the basis for obtaining the impedance values.

The method may further comprise periodically regenerating the impedance model based on a selected subsequently delivered charge pulse. The method may further comprise using an adjustment model to adjust the pulse width or quantum of charge to be delivered according to the impedance model.

Some embodiments relate to a method for controlling delivery of stimulation signals, comprising:
controlling delivery of at least one initial charge pulse via the stimulation delivery circuit based on a first control parameter;
controlling delivery of at least one subsequent charge pulse via the stimulation delivery circuit based on a second control parameter; and
modifying the controlled delivery of the at least one subsequent charge pulse based on an adjustment model.

The modifying may include increasing or decreasing at least one pulse width of the at least one subsequent charge pulse based on the adjustment model. The first control parameter may be constant current control and the second control parameter may be voltage control. Alternatively, the first control parameter may be voltage control and the second control parameter may be constant current control.

The controlling delivery of the at least one subsequent charge pulse may be performed based on an impedance model. The method may further comprise generating the impedance model based on measured voltage and controlled current delivery via the stimulation delivery circuit during the at least one initial charge pulse.

Some embodiments relate to a method of controlling delivery of stimulation signals, comprising:
controlling delivery of at least one charge pulse via a stimulation delivery circuit based on an impedance model of a plurality of stimulation electrodes; and
modifying the controlled delivery of the at least one charge pulse based on an adjustment model.

The adjustment component may modify delivery of the at least one charge pulse by increasing or decreasing at least one pulse width of the at least one charge pulse.

Some embodiments relate to a method for controlling delivery of stimulation signals, comprising:
generating an electrode impedance model for each of a plurality of sets of stimulation electrodes based on at least one initial charge pulse provided to each respective set of stimulation electrodes; and
controlling provision of at least one subsequent charge pulse to one or more of the plurality of sets of stimulation electrodes based on the respective electrode impedance model generated for the one or more sets of stimulation electrodes.

Control of voltage and current in the context of charge pulse control and delivery as described herein is intended to include control of the magnitude of the voltage or current as well as the polarity and pulse width of the voltage- or current-driven charge pulse.

BRIEF DESCRIPTION OF THE DRAWINGS

Embodiments are described in further detail below, by way of example and with reference to the accompanying drawings, in which.

DETAILED DESCRIPTION

Figure 1:
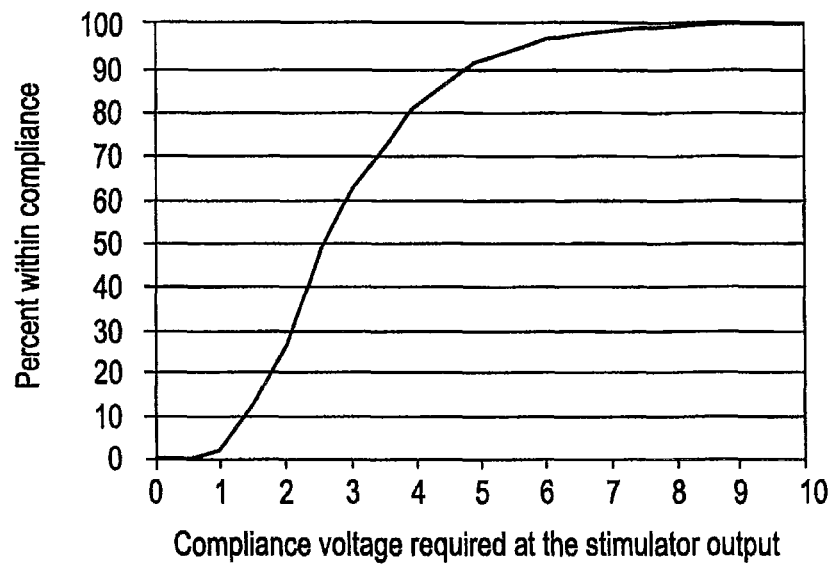
FIG. 1 is a graph of compliance voltage required at a stimulator output versus percentage within compliance for certain existing biphasic current stimulation devices.

Described, embodiments generally relate to devices, circuitry, prostheses and methods for controlling delivery of stimulation signals, such as nerve stimulation signals. In described embodiments, stimulation to be delivered by the described devices and/or circuitry is generally intended to be delivered subcutaneously, rather than transcutaneously. However, the principles of operation of described embodiments are applicable to other modes of electrical stimulation of different kinds of excitable human and/or animal tissue.

In some embodiments, the stimulation signals may be generated based on an external stimulus, such as an auditory or visual stimulus. However, in some embodiments, the stimulation signals may alternatively or additionally be generated responsive to sensed internal physiological conditions or to a predetermined timing sequence accessible to a processor of the device.

Embodiments have particular applicability to biphasic current stimulation regimes and this is therefore the context in which embodiments are generally described. However, the emphasis throughout on biphasic stimulation should not be construed to limit the generalisation of the disclosure; the same functional concepts apply well to monophasic or triphasic or other stimulation waveforms. In each case, charge balance is required at each electrode and can be achieved by known techniques. The provision of charge pulses may therefore be described in terms of charge-balanced pulsatile stimulation, independent of how many phases are used to deliver the stimulation.

Certain evidence suggests that neurons can be caused to produce action potentials in essentially the same way with either constant-voltage or constant-current electrical pulses. Constant-current stimulation is conventional in cochlear implants (CIs), and is becoming an accepted type of stimulation for other neural stimulators (such as the implantable pulse generators used in Deep Brain Stimulation). However, constant-voltage stimulation may be more efficient in electrical terms.

One reason for preferring constant current stimulation is that it seems likely that the intended outcomes of the stimulation (such as perception of a hearing sensation with a cochlear implant) will be less affected by changes in the impedance of the electrode-neural interface. Such changes are common for implanted electrodes and can encompass a very wide range of impedances (at least one order of magnitude). Impedances vary not only among electrodes but also over time. Therefore, some described embodiments provide a method and means for applying constant-voltage stimulation with outcomes that are not substantially affected by changes in electrode impedance, or at least periodically adapted to account for such changes.

Particular embodiments described herein are configured to provide monitoring and control functionality for stimulation devices, whereby one or more components are configured to monitor the charge delivered by a stimulation signal generating component in at least one initial charge pulse and to then take action to ensure that the intended charge (or near enough thereto) is actually delivered in subsequent charge pulses. In some embodiments, this is accomplished by monitoring the initial charge delivered using constant current and using the delivered current waveform in combination with the measured electrode voltage waveform to generate an impedance model. Subsequent charge delivery is then performed using that model but based on voltage control, rather than current control.

Figure 2:
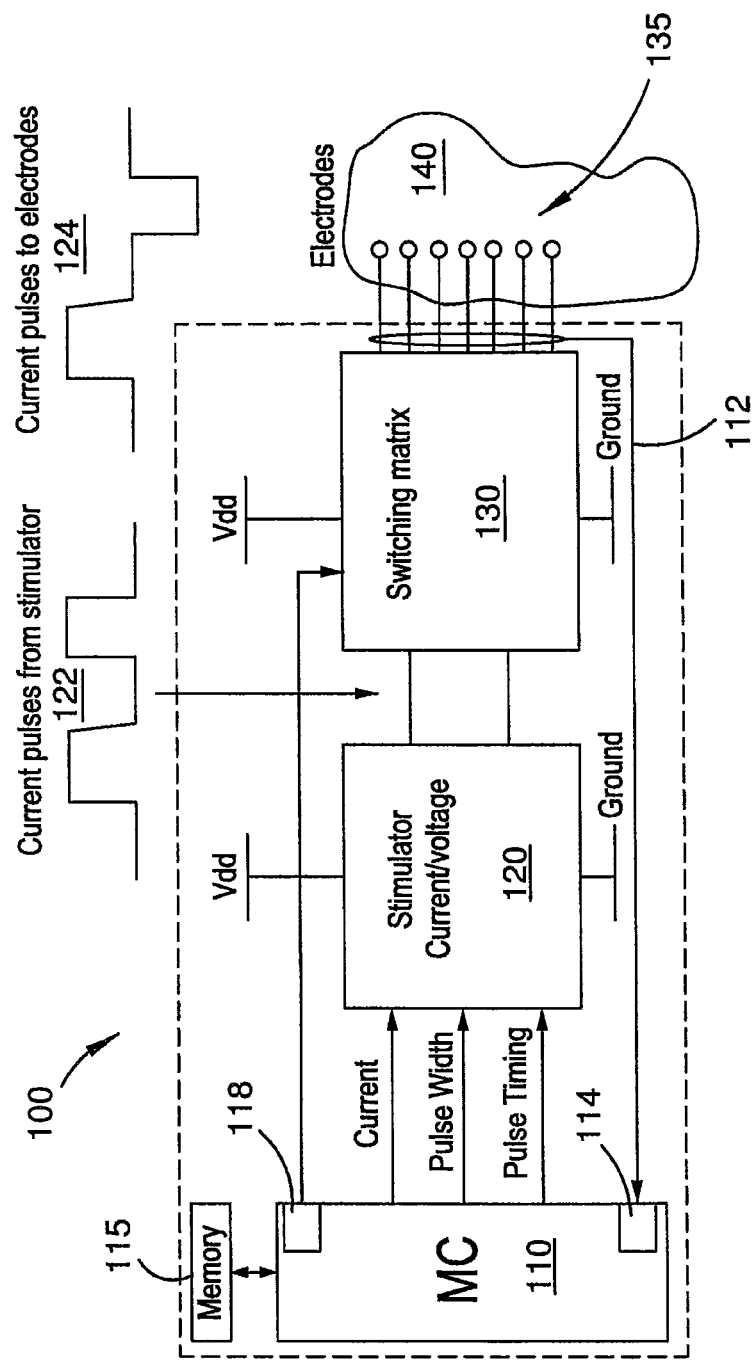
FIG. 2 is a schematic illustration of a device for generating stimulation signals as part of a prosthesis.
Figure 5:
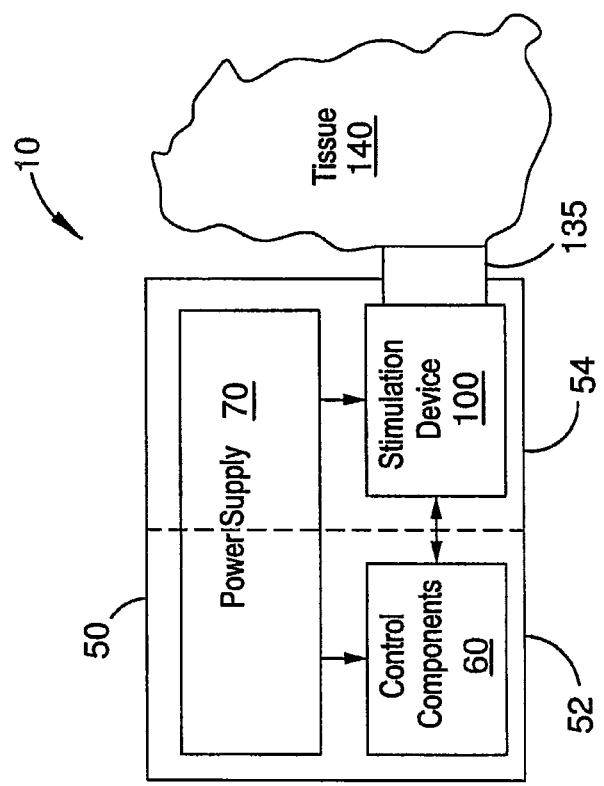
FIG. 5 is a schematic diagram of a stimulation system including a prosthesis that comprises the device of FIG. 2.

Referring in particular to FIGS. 2 and 5, a stimulation device 100 is shown and described in further detail. Device 100 may also be considered as a system of component's and circuits and as part of a larger stimulation system 10. Device 100 has a microcontroller 110 that provides current, pulse width and pulse timing signals to a stimulation circuit 120, which in turn provides electrical output signals 122 (in the form of a charge pulse waveform) to switching matrix 130 for delivery of the electrical signals in biphasic form 124 to a tissue or tissue region 140 via electrodes 135 embedded in or contacting the tissue 140. Stimulation circuit 120 thus acts as a stimulation signal generation circuit and switching matrix 130 thus acts as a stimulation signal delivery circuit.

Microcontroller 110 is referenced as one non-limiting example of an electronic control component that can be used to perform the functions described herein. Other examples of possibly suitable electronic control components to perform the described functions include, but are not limited to, a microprocessor, a digital signal processor, an application-specific integrated circuit (ASIC), a state machine, a field-programmable gate array (FPGA) or a combination of any of those devices with microcontroller 110 or a combination of any two or more of such devices.

Stimulation device 100 may form part of a prosthesis 50 or other device (FIG. 5) for providing nerve stimulation to nerves in the tissue 140. For convenience, the term prosthesis will be used herein in relation to reference numeral 50, but it is to be understood that reference numeral 50 may represent devices or parts thereof that do not strictly act as a prosthesis or part thereof.

The prosthesis 50 may form part of a stimulation system 10 and may include other components, such as control components 60 and power supply 70, interacting with the prosthesis 50 in order to provide appropriate control functions and power to the prosthesis 50. Power supply 70 provides power to stimulation device 100 and control components 60. Each of microcontroller 110, stimulation circuit 120 and switching matrix 130 may be coupled to a voltage supply rail Vdd and to a ground rail. The supply voltage Vdd is derived from electrical potential supplied by the power supply 70. Alternatively, microcontroller 110 may supply power to stimulation circuit 120 or control the supply of power to stimulation circuit 120 by power supply 70.

In some embodiments, the prosthesis 50 may be generally contained by a unitary housing. In other embodiments, the prosthesis 50 may comprise an implantable part 54 and a non-implantable part 52. In such two-part embodiments, the implantable part 54 includes the stimulation device 100 and at least part of power supply 70. The power supply 70 may be either self-contained or one part of a two-part power supply.

Such a two-part power supply includes a power source, such as a battery, in a first part arranged to inductively transfer power to the second part and is advantageous for two-part prostheses where it is preferred to avoid having a power source in the part to be implanted. Thus, the part of power supply 70 that is in implantable part 54 may be inductively driven by an external coil in the non-implantable part 52 that houses the remainder of power supply 70. In two-part prosthesis embodiments, the control components 60, which may be used to configure stimulation settings for example, may be divided between the two parts 52, 54, with communication between the two effected by suitable communication means, preferably wirelessly.

Although some device configurations are described, various other configurations are possible. For example, the electronics could be outside and the electrodes inside the body, with a hard-wired connector linking them. Similarly, there are various ways of powering such devices. Thus, the described arrangements are intended to be exemplary and non-limiting.

The prosthesis or assistive device 50 may be employed to provide stimulation to sensory nerves, for example as part of an auditory or visual prosthesis, or to provide myoelectric stimulation for muscle activation, for example as part of a cardiac prosthesis. The prosthesis or assistive device 50 may be arranged for stimulation of a selected part of the brain, for example to modulate, hinder or otherwise beneficially affect movement disorders, psychiatric disorders, seizures or potential seizures. Such seizures may be associated with epilepsy or Parkinson's disease, for example.

The microcontroller 110 of stimulation device 100 may comprise any suitable processing device for receiving input signals, processing stored instructions and generating suitable output signals, such as current, pulse width and pulse timing signals. The microcontroller 110 has suitable volatile memory 115 and has (or at least has access to) non-volatile memory (also shown as 115 for simplicity) storing program code executable by the microcontroller 110 to perform the functions described herein. Such program code may be arranged as a plurality of code modules to perform certain functions, such as the monitoring, model generation and charge delivery control functions described herein.

Stimulation circuit 120 may be a standard constant-current stimulation circuit.

Some embodiments rely on microcontroller 110 to monitor delivery of the current levels at the output of switching circuit 130 during transmission of the stimulation pulse and use the monitored delivered current waveform to develop an impedance model 300. In other embodiments, microcontroller 110 may use a specified current as the basis for developing the impedance model 300, on the assumption that the output current levels will closely match the specified current levels.

Microcontroller 110 also measures the output voltage waveform at the output electrodes 135 via a sampling circuit 112 that is coupled to an analogue to digital converter (ADC) 114 in communication, or integral with, microcontroller 110 and arranged to sense the electrical potential at the electrodes 135.

Figure 3:
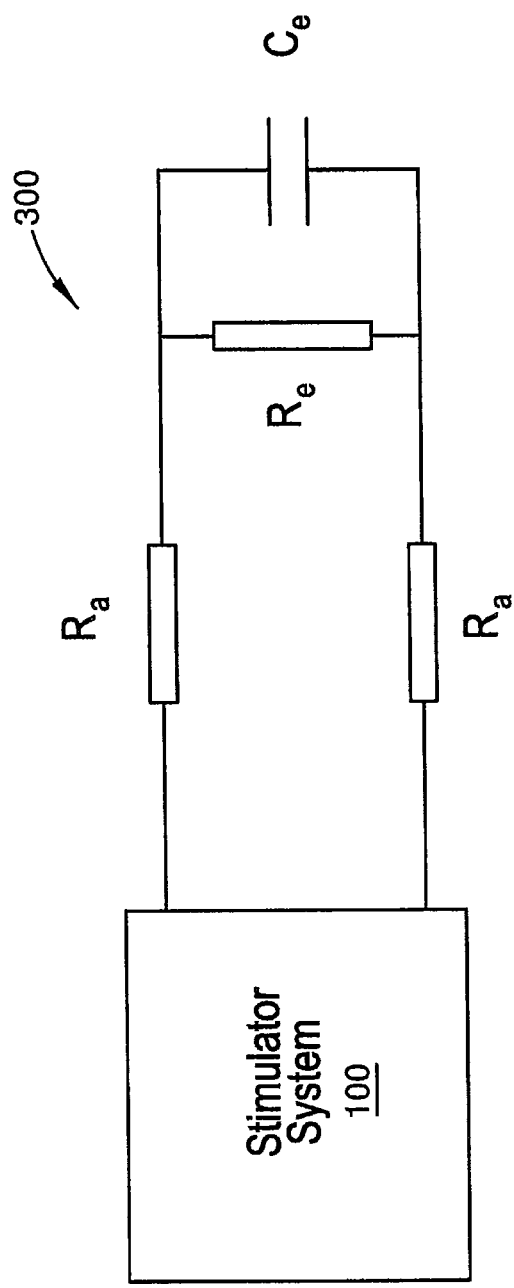
FIG. 3 is a schematic representation showing a simple electrical model of electrode impedance when an electrode circuit is connected to a stimulation device during delivery of stimulation signals.
Figure 4:
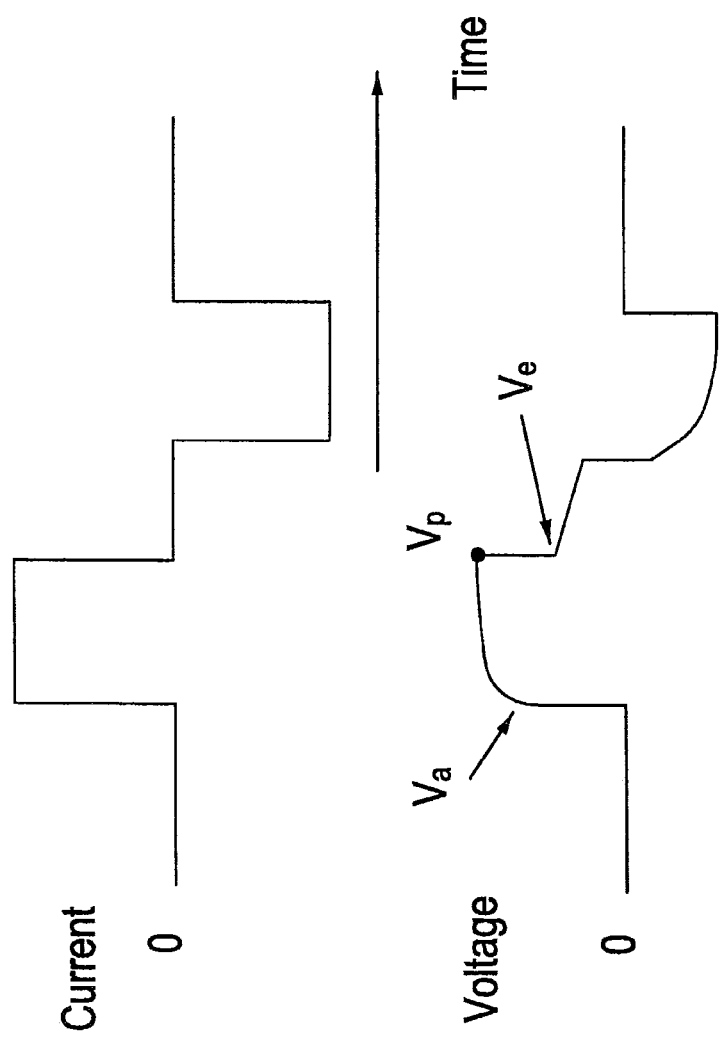
FIG. 4 is an illustration of example current and voltage waveforms during delivery of a biphasic constant-current pulse to an electrode circuit.

FIG. 3 is a circuit diagram showing an example electrical model of an electrode pair. The stimulator system may deliver biphasic current pulses to the electrodes as illustrated in the upper part of FIG. 4. The corresponding voltage waveform across the electrodes is shown in the lower part of FIG. 4. In the stimulation device 100, the voltage waveform is sampled and converted into digital values (with a sampling rate and voltage resolution high enough to capture all relevant details of the waveform). As mentioned above, the microcontroller may measure the output current at electrodes 135. Alternatively, the microcontroller 110 may "know" the parameters of the current waveform delivered to the electrodes via stimulation circuit 120 and switching matrix 130 because it provides the control signals to effect the delivery of the current waveform. With these two sets of data (i.e. current and voltage), the electrode impedance can be estimated.

First, a sufficiently accurate electrical model is chosen, such as that shown in FIG. 3. This model 300 consists only of a RC circuit including resistors (Ra, Re) and capacitors that have constant values. The values can be estimated by means of relatively simple computations using the data representing the current and voltage waveforms. For example, the voltage Va, occurring at the onset of the current, and indicated in the lower part of FIG. 4, allows the resistance Ra to be calculated as:

$$Ra = 0.5 * (Va/Ie),$$

where Ie is the electrode current.

The voltage Vp, occurring immediately before the end of the first phase of current delivery (FIG. 4), can be used to calculate a quantity known conventionally as the "electrode impedance" (i.e., Vp/Ie). The voltage Ve, occurring immediately after the end of the first phase of current delivery, is a measure of the voltage retained on the capacitor Ce (FIG. 3) at that time. Between the two phases of current delivery there is usually a brief "gap" during which no current is delivered to the electrodes by the stimulator circuit. The decay of the electrode voltage during the gap is determined by the values of Re and Ce; i.e., the time constant of that voltage decay is Re*Ce. Using these measures, the values of Ra, Re, and Ce can be estimated.

For model 300, the time-varying electrode voltage V(t) for a constant electrode current Ie is given by:

$$2 * Ie * Ra + Ie * Re * (1 - e^{-\frac{t}{Re*Ce}})$$

where t is time during the first phase of the current pulse.

Figure 6:
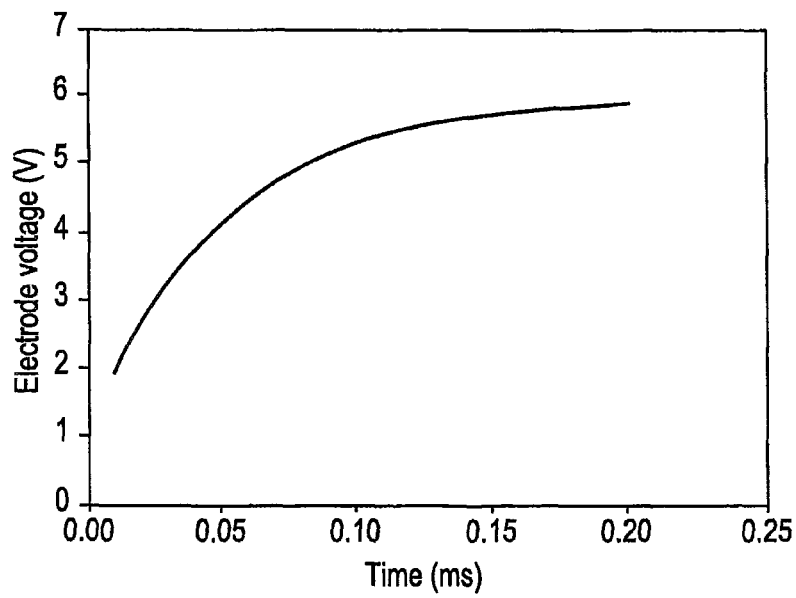
FIG. 6 is a graph of an illustrative example of part of a voltage curve for a stimulation pulse.

With example component values: Ra=500Ω; Re=5000Ω; Ce=10 nF; and Ie=1 mA, the voltage waveform during part of first phase of a biphasic constant-current pulse) looks like the voltage curve shown in the graph of voltage over time in FIG. 6. As is shown in the graph of FIG. 6, the pulse width of the first phase may be in the order of 0.2 ms. These example values should be understood to be provided strictly for purposes of illustration, without limitation. Different stimulation parameters and impedance model values may be employed for each application and circumstance.

Although the illustrated model 300 of the electrical characteristics of an electrode circuit would be adequate in many applications, more complex impedance models exist that enable a closer approximation to the electrode behaviour to be calculated by addition of further resistances and capacitances (or other elements) into the model circuit. In general, any such model enables a voltage waveform to be predicted for any given (typically constant-current) stimulation waveform. The model parameters need to be estimated in such a way as to maximise the accuracy of the prediction. There are known computation methods that achieve such estimations. These methods start with an equation relating the voltage to the current in terms of the values of the model components. The parameters of the equation (i.e., the model component values) are adjusted iteratively such that the predicted voltage waveform eventually approximates closely the measured voltage waveform.

For example, one well-established and reliable technique is the Marquardt-Levenberg algorithm. This algorithm seeks the values of the parameters that minimise the sum of the squared differences between the values of the observed and predicted values of the dependent variable in the equation (i.e., the voltage waveform). The seeking process is iterative; the algorithm begins with a guess at the parameters, checks to see how well the equation fits, then continues to make better guesses until the differences between the residual sum of squares no longer decreases significantly. This condition is known as convergence. Once convergence has been achieved, the parameter values are taken as good estimates of the true component values in the model 300 and are stored in memory 115. Microcontroller 110 then calculates the pulse duration and/or constant voltage level to be applied by microcontroller 110 to switching matrix 130 in delivering subsequent charge pulses via electrodes 135.

According to embodiments employing microcontroller 110 to determine an impedance model and then provide voltage-controlled stimulation delivery, microcontroller 110 may be considered to comprise a monitoring component, a model generation component and a stimulation control component. The monitoring component measures (or specifies) delivered current and measures the resulting electrode voltage in an initial (or periodically selected subsequent) waveform and the model generating component develops an impedance model based on those measurements. The stimulation control component delivers subsequent stimulation waveforms by controlling the provision of a voltage output waveform at the electrodes 135 to achieve the intended charge delivery based on the impedance model 300. These monitoring, model generation, and stimulation control components may be effected by code modules stored in memory 115 accessible to microcontroller 110 such that, when such code modules are executed by microcontroller 110, the microcontroller 110 is configured to perform the charge delivery control and modelling functions described.

The described techniques may be used as an extension of a conventional constant-current stimulator. The extension enables the stimulator circuit to be switched from the constant-current mode to a constant-voltage mode once the model 300 has been generated. The latter mode would typically involve connecting the electrode circuit (i.e. switching matrix 130) directly to a (constant-voltage) power supply 118 provided as an output of microcontroller 110, which receives its power from power supply 70, as it can be assumed that this will maximise overall energy efficiency. However, some embodiments may alternatively employ stimulation circuit 120, under the control of microcontroller 110, to generate stimulation signals for delivery to the tissue via the switching matrix 130.

In order to generate the model 300, stimulation device 100 uses the sampling circuit 112 as a means for measuring each electrode voltage in real time. The sampling circuit 112 provides the sampled analogue signals to the ADC 114, which is either part of microcontroller 110 or separate but in communication therewith.

Memory 115 is used for storing the model 300 (or another suitable model) of electrode impedance as a basis for effecting charge delivery. Additionally, memory 115 may store an empirically derived adjustment model to account for the effects on the desired stimulation outcome of changing the pulse width of the stimuli, which is described further below. The term "stimulation outcome" is used to mean the intended hearing percepts, or some equivalent effect for other therapeutic applications of stimulation. The adjustment model can be used to adjust the pulse width of the constant voltage waveform providing the desired charge pulse. For example, the voltage stimulation pulse may be shortened or lengthened by a predetermined percentage amount, such as 5% to 10%, specified in the model for the magnitude of the voltage to be delivered.

An exemplary method of operation of the stimulation device 100 is as follows:

1. Using the conventional constant-current mode, the relationship is established between the desired stimulation outcome and the physical parameters of the stimuli. For example, in a cochlear implant (CI), the current levels and pulse widths are found for each electrode that encompass the range between the threshold of hearing and the maximum desirable loudness. This procedure may be the same as that employed with conventional CI systems.

2. While stimulating in the constant-current mode, the microcontroller 110 may automatically measure the voltage waveform on each electrode 135 using sampling circuit 112. Using those measurements and measured or known data describing the (constant-current) stimuli, the microcontroller 110 determines the parameter values for a numerical model, such as model 300, of each electrode's electrical (impedance) characteristics, either with reference to a common reference voltage or with reference to one or more other electrodes. The electrodes may thus be configured to provide stimulus currents between each other in a one-to-one, one-to-many or many-to-one relationship. In some embodiments, the numerical impedance model may be generated based on known or measured voltage-driven stimulus while measuring (by sampling) the output current. However, for purposes of illustration, it is assumed that the model is generated based on measured or known data describing the constant-current stimuli and sampled voltage, for use in subsequently delivering constant-voltage stimulation.

The numerical impedance model for each set of one or more electrodes is intended to provide an accurate relationship between the current delivered to the one or more electrodes and the resulting voltage on the one or more electrodes. Such numerical models may be linear and comprise 1-2 capacitors in parallel and/or series combination with 2-3 resistors, for example. The values of the model's impedance components require estimation as described above to enable the subsequent steps to be completed.

3. Once the generation of the model 300 is complete, the microcontroller 110 automatically uses the model 300 to calculate the voltage pulse width required to achieve the same stimulation outcome when using the constant-voltage stimulation mode (at a known or measured voltage level). Microcontroller 110 then switches to the constant-voltage-stimulation mode, and, by using the model 300, varies the pulse width in subsequent stimulation pulses (in a train of such pulses) to achieve the intended stimulation outcome. The stimulation outcome should be very similar to that obtained when constant-current stimulation was used.

4. The constant voltage pulse width may be adjusted before the charge pulse is delivered to the electrodes 135. In general, the pulse widths will be narrower in constant-voltage mode after the procedure of step 3 has been applied. This is because the voltage applied to the electrodes will typically be higher in the constant-voltage mode than occurred during the constant-current mode for the same intended stimulation outcome, leading to a higher current on average, and therefore requiring a narrower pulse width to deliver approximately the same charge to the electrodes. This is one of the main reasons for the improved efficiency. In some situations where the supply voltage is set to a relatively low level, the pulse widths in the constant-voltage mode may be wider. Note that the first and second phases of a biphasic constant-voltage pulse are not necessarily equal in duration to achieve charge balance, and the knowledge of the resistor and capacitor components of the impedance model will assist in adjusting one or both of the two phases appropriately to maintain desired charge balance.

Unfortunately, when the pulse width is changed, the same stimulation outcome cannot always be guaranteed even when the stimuli contain the same charge. However, an empirically derived stimulation outcome adjustment model can be used to predict how the charge should be varied (e.g. by reducing or increasing the pulse width by a predetermined percentage) in order to maintain the same stimulation outcome when the pulse width is changed. Such an adjustment model can be used to improve the stimulation outcome accuracy of the pulse width calculated in step 3.

5. As electrode impedances can vary over time, the above steps 2-4 may need to be repeated by microcontroller 110 periodically to regenerate the model for constant voltage-based charge delivery. To do this, the microcontroller 110 switches back to constant-current mode for delivery of one or more charge pulses so that a new impedance model can be generated for each set of electrodes and the constant-voltage stimulation mode can again be resumed based on the newly generated impedance model. Periodic regeneration of the model is intended to ensure that the electrical models 300 of the electrode impedance reasonably accurately represent the electrodes' true impedance characteristics. The periodic regeneration of the model may be programmed into microcontroller 110 and memory 115 to occur at fixed time intervals. Alternatively or in addition, the periodic regeneration could be programmed to occur each time the device is switched on by the user, and/or each time a different user program is selected, and/or each time the system is adjusted in a routine maintenance schedule.

As the stimulation outcomes are likely to be very similar for the constant-current and constant-voltage modes, the replacement of constant current stimulation with constant voltage stimulation should not disrupt the recipient's use of the device.

The stimulation voltage in the constant-voltage mode may be, on average, lower than the power-supply voltage used in the conventional constant-current mode, which may enable further energy-efficiency gains.

Charge balance at the electrodes, which is required for safe chronic stimulation, can be achieved with the described embodiments in at least two ways: (1) by using the model-based calculations to determine what pulse width is required for the second phase of each biphasic stimulus to cancel exactly the charge delivered in the first phase; and (2) by placing a capacitor (not shown) in series with at least one of the electrodes 135 in each active electrode circuit and shorting-out the circuit (including the capacitor) at the end of each stimulus pulse.

Advantageously, the increase in circuit complexity for described embodiments relative to a conventional constant-current implantable stimulator is very slight. Most of the required circuitry is already present in existing implants. Further, there is no requirement for precise electronic components, accurate matching between components, or circuits with specifications that are difficult to achieve (e.g., voltage comparators that are very fast).

However, the model generation procedure may need to be activated frequently if there is evidence (or a likelihood) that the electrode impedance changes frequently over a wide range. Also, use of a purely constant-voltage mode of stimulation may lead to a high spike in the electrode current at the onset of each pulse. If this is undesirable (e.g., because of safety concerns), then known techniques are available to minimise any excessive current.

The described embodiments offer a simple way in which the average supply voltage (and thus power) of a stimulation circuit can be significantly reduced, while maintaining the desired stimulation levels.

The invention claimed is:

1. A device for controlling delivery of stimulation signals, comprising:
   a stimulation delivery circuit;
   a monitoring component to monitor the waveform of the voltage supplied in at least one current-driven charge pulse via the stimulation delivery circuit;
   a stimulation control component to control the waveform of the voltage supplied in at least one subsequent voltage-driven charge pulse based on the charge of the at least one current-driven charge pulse delivered by the stimulation delivery circuit; and
   a model generation component to generate an impedance model of stimulation electrodes in the stimulation delivery circuit, wherein the stimulation control component is configured to control the stimulation delivery circuit to deliver charge according to the impedance model,
   wherein the impedance model is a RC circuit impedance model.

2. The device of claim 1, wherein the model generation component is configured to generate the impedance model based on measured voltage and controlled current delivery via the stimulation delivery circuit during the at least one charge pulse.

3. The device of claim 1, wherein the model generation component is configured to periodically regenerate the impedance model based on a selected subsequently delivered charge pulse.

4. The device of claim 1, wherein the model generation component is configured to generate an impedance model in respect of each of a plurality of sets of electrodes, where each set of electrodes includes one or more electrodes.

5. The device of claim 1, further comprising a processor, wherein the monitoring component and stimulation control component comprise code modules accessible to the processor and executable by the processor, and wherein the processor is configured to control delivery of charge by the stimulation delivery circuit.

6. A device for controlling delivery of stimulation signals, comprising:
   a stimulation delivery circuit;
   a monitoring component to monitor the waveform of the voltage supplied in at least one current-driven charge pulse via the stimulation delivery circuit;
   a stimulation control component to control the waveform of the voltage supplied in at least one subsequent voltage-driven charge pulse based on the charge of the at least one current-driven charge pulse delivered by the stimulation delivery circuit; and
   a model generation component to generate an impedance model of stimulation electrodes in the stimulation delivery circuit, wherein the stimulation control component is configured to control the stimulation delivery circuit to deliver charge according to the impedance model,
   wherein the model generation component is configured to use an adjustment model to adjust the pulse width or quantum of charge to be delivered according to the impedance model.

7. The device of claim 6, wherein the model generation component is configured to generate the impedance model based on measured voltage and controlled current delivery via the stimulation delivery circuit during the at least one charge pulse.

8. A device for controlling delivery of stimulation signals, comprising:
- a stimulation delivery circuit;
- a monitoring component to monitor the waveform of the voltage supplied in at least one current-driven charge pulse via the stimulation delivery circuit;
- a stimulation control component to control the waveform of the voltage supplied in at least one subsequent voltage-driven charge pulse based on the charge of the at least one current-driven charge pulse delivered by the stimulation delivery circuit;
- a model generation component to generate an impedance model of stimulation electrodes in the stimulation delivery circuit, wherein the stimulation control component is configured to control the stimulation delivery circuit to deliver charge according to the impedance model; and
- a processor, wherein the model generation component comprises a code module accessible to the processor and executable by the processor.

9. The device of claim 8, wherein the monitoring component and stimulation control component comprise code modules accessible to the processor and executable by the processor, and wherein the processor is configured to control delivery of charge by the stimulation delivery circuit.

10. The device of claim 8, wherein the model generation component is configured to periodically regenerate the impedance model based on a selected subsequently delivered charge pulse.

11. The device of claim 8, wherein the model generation component is configured to generate the impedance model based on measured voltage and controlled current delivery via the stimulation delivery circuit during the at least one charge pulse.

12. The device of claim 8, wherein the device is configured for use as part of a prosthesis.

13. The device of claim 12, wherein the prosthesis is a sensory prosthesis.

14. The device of claim 12, wherein the prosthesis is an implantable or partially implantable prosthesis.

15. The device of claim 8, wherein the device is an implantable or partially implantable brain stimulation device.

16. The device of claim 8, wherein the device is an implantable or partially implantable stimulation device.

17. A prosthesis comprising the device of claim 8.

18. The device of claim 8, wherein the model generation component is configured to generate an impedance model in respect of each of a plurality of sets of electrodes, where each set of electrodes includes one or more electrodes.

19. A device for controlling delivery of stimulation signals, comprising:
- a stimulation delivery circuit;
- a control component to control delivery of a waveform of at least one initial charge pulse via the stimulation delivery circuit based on a first control parameter and to control delivery of a waveform of at least one subsequent charge pulse via the stimulation delivery circuit based on a second control parameter; and
- an adjustment component to modify controlled delivery of a quantum of charge delivered by the at least one subsequent charge pulse based on an adjustment model;
  - wherein the at least one initial charge pulse is one of current-driven and voltage-driven, and wherein if the at least one initial charge pulse is current-driven, then the at least one subsequent charge pulse is voltage-driven, and if the at least one initial charge pulse is voltage-driven, then the at least one subsequent charge pulse is current-driven,
  - wherein the adjustment component modifies delivery of the at least one subsequent charge pulse by increasing or decreasing at least one pulse width of the at least one subsequent charge pulse.

20. A device for controlling delivery of stimulation signals, comprising:
- a stimulation delivery circuit;
- a control component to control delivery of at least one charge pulse via the stimulation delivery circuit based on an impedance model of a plurality of stimulation electrodes; and
- an adjustment component to modify controlled delivery of the at least one charge pulse based on an adjustment model;
- wherein the adjustment component modifies delivery of the at least one charge pulse by increasing or decreasing at least one pulse width of the at least one charge pulse.

* * * * *